(12) United States Patent
Lu et al.

(10) Patent No.: US 9,382,557 B2
(45) Date of Patent: Jul. 5, 2016

(54) YEAST STRAIN FOR LACTIC ACID PRODUCTION BY USING PENTOSE AND HEXOSE

(71) Applicant: FAR EASTERN NEW CENTURY CORPORATION, Taipei (TW)

(72) Inventors: Li-Ting Lu, Taipei (TW); Der-Ren Hwang, Taipei (TW)

(73) Assignee: FAR EASTERN NEW CENTURY CORPORATION, Taipei (TW)

( * ) Notice: Subject to any disclaimer, the term of this patent is extended or adjusted under 35 U.S.C. 154(b) by 191 days.

(21) Appl. No.: 14/108,825

(22) Filed: Dec. 17, 2013

(65) Prior Publication Data

US 2014/0342415 A1   Nov. 20, 2014

(30) Foreign Application Priority Data

Mar. 29, 2013   (TW) .............................. 102111616 A

(51) Int. Cl.
| | | |
|---|---|---|
| *C12N 1/18* | (2006.01) |
| *C12P 7/56* | (2006.01) |
| *C12N 15/81* | (2006.01) |
| *C12R 1/865* | (2006.01) |
| *C12N 9/04* | (2006.01) |

(52) U.S. Cl.
CPC .................. *C12P 7/56* (2013.01); *C12N 9/0006* (2013.01); *C12N 15/81* (2013.01); *C12R 1/865* (2013.01); *C12Y 101/01027* (2013.01); *C12P 2203/00* (2013.01); *Y02P 20/52* (2015.11)

(58) Field of Classification Search
CPC ....................................................... C12N 1/18
USPC ..................................................... 435/252.3
See application file for complete search history.

(56) References Cited

U.S. PATENT DOCUMENTS

| | | | |
|---|---|---|---|
| 5,789,210 A | 8/1998 | Ho et al. |
| 7,109,010 B2 | 9/2006 | Rajgarhia et al. |
| 7,141,410 B2 | 11/2006 | Rajgarhia et al. |
| 7,943,366 B2 | 5/2011 | Rajgarhia et al. |
| 2004/0029238 A1 | 2/2004 | Rajgarhia et al. |

FOREIGN PATENT DOCUMENTS

| | | |
|---|---|---|
| CN | 1367841 A | 9/2002 |
| CN | 101463328 A | 6/2009 |
| CN | 102212489 A | 10/2011 |
| CN | 101886048 B | 5/2012 |

OTHER PUBLICATIONS

Sylvie Dequin et al.; Mixed Lactic Acid-Alcoholic Fermentation by *Saccharomyes cerevisiae* Expressing the *Lactobacillus casei* L(+)-LDH; Biotechnology (New York), Feb. 1994, 12:p. 173-177.
Haruo Takahashi et al.; Efficient Production of L-Lactic Acid by Metabolically Engineered *Saccharomyces cerevisiae* with a Genome-Integrated L-Lactate Dehydrogenase Gene; Biosci Biotechnol Biochem. May 2006; 70 (5): 1148-53.
Haruo Takahashi et al.; The Effect of Pyruvate Decarboxylase Gene Knockout in *Saccharomyces cerevisiae* on L-Lactic Acid Production; Applied and Environmental Microbiology, Apr. 2005, p. 1964-1970.
Johannes H. Hegemann et al.; A new efficient gene disruption cassette for repeated use in budding yeast; Nucleic Acids Research, 1996, vol. 24, No. 13 2519-2524.
Search Report dated Aug. 11, 2014 for Taiwanese Application No. 102111616.
Espacenet English abstract of CN 101886048 B.
Ishida, N., et al., "Efficient Production of L-Lactic Acid by Metabolically Engineered *Saccharomyces cerevisiae* with a Genome-Integrated L-Lactate Dehydrogenase Gene", Appl. Environ. Microbiol, Apr. 2005 71(4), pp. 1964-1970.
Jeffries, T. W., et al., "Metabolic engineering for improved fermentation of pentoses by yeasts", Appl. Microbio. Biotechnol., Feb. 2004 63(5), pp. 495-509.
Tamakawa, H., et al., "Efficient production of L-lactic acid from xylose by a recombinant *Candida utilis* strain", J. Biosci. Bioeng., Jan. 2012 113(1), pp. 73-75.
English translation of a Search Report dated Oct. 23, 2015 for Chinese Application No. 201310288914.8.
Espacenet English abstract of CN 102212489 A.
Espacenet English abstract of CN 101463328 A.

*Primary Examiner* — Maryam Monshipouri
(74) *Attorney, Agent, or Firm* — Ladas & Parry LLP

(57) ABSTRACT

The present invention provides a biologically pure culture of *Saccharomyces cerevisiae*, which culture has a characteristic nature capable of highly producing lactic acid. A method for preparing the biologically pure culture and a method for production of lactic acid are also provided.

11 Claims, 5 Drawing Sheets

SEQUENCE LISTING

<160> NUMBER OF SEQ ID NOS: 35

<210> SEQ ID NO 1
<211> LENGTH: 37
<212> TYPE: DNA
<213> ORGANISM: ARTIFICIAL SEQUENCE
<220> FEATURE:
<223> OTHER INFORMATION: Primer

<400> SEQUENCE: 1
gactacgcat gcggcgcgaa tcctttattt tggcttc                37

<210> SEQ ID NO 2
<211> LENGTH: 46
<212> TYPE: DNA
<213> ORGANISM: ARTIFICIAL SEQUENCE
<220> FEATURE:
<223> OTHER INFORMATION: Primer

<400> SEQUENCE: 2
tgaattactg aacacaacat tgttttatat ttgttgtaaa aagtag        46

<210> SEQ ID NO 3
<211> LENGTH: 37
<212> TYPE: DNA
<213> ORGANISM: ARTIFICIAL SEQUENCE
<220> FEATURE:
<223> OTHER INFORMATION: Primer

<400> SEQUENCE: 3
gactctcatc taaattgaat tgaattgaaa tcgatag                37

<210> SEQ ID NO 4
<211> LENGTH: 61
<212> TYPE: DNA
<213> ORGANISM: ARTIFICIAL SEQUENCE
<220> FEATURE:
<223> OTHER INFORMATION: Primer

<400> SEQUENCE: 4
tagagtcccg ggagtctgct cgaggagatg cggccgcgac ttttttttgtt gcaagtggga    60
t                                                                    61

<210> SEQ ID NO 5
<211> LENGTH: 30
<212> TYPE: DNA
<213> ORGANISM: ARTIFICIAL SEQUENCE
<220> FEATURE:
<223> OTHER INFORMATION: Primer

<400> SEQUENCE: 5
aaaacaatgc cttctattaa gttgaactct                                      30

<210> SEQ ID NO 6
<211> LENGTH: 38
<212> TYPE: DNA
<213> ORGANISM: ARTIFICIAL SEQUENCE
<220> FEATURE:
<223> OTHER INFORMATION: Primer

<400> SEQUENCE: 6
caattcaatt caatttagac gaagatagga atcttgtc                             38

<210> SEQ ID NO 7
<211> LENGTH: 39
<212> TYPE: DNA
<213> ORGANISM: ARTIFICIAL SEQUENCE
<220> FEATURE:
<223> OTHER INFORMATION: Primer

<400> SEQUENCE: 7
gactacgcgg ccgcggcgcg aatcctttat tttggcttc                            39

<210> SEQ ID NO 8
<211> LENGTH: 46
<212> TYPE: DNA
<213> ORGANISM: ARTIFICIAL SEQUENCE
<220> FEATURE:
<223> OTHER INFORMATION: Primer

<400> SEQUENCE: 8
aaggaagggt tagcagtcat tgttttatat ttgttgtaaa aagtag                    46

<210> SEQ ID NO 9
<211> LENGTH: 29
<212> TYPE: DNA
<213> ORGANISM: ARTIFICIAL SEQUENCE
<220> FEATURE:
<223> OTHER INFORMATION: Primer

<400> SEQUENCE: 9
aaaacaatgt tgtgttcagt aattcagag                                       29

<210> SEQ ID NO 10
<211> LENGTH: 39
<212> TYPE: DNA
<213> ORGANISM: ARTIFICIAL SEQUENCE

```
<220> FEATURE:
<223> OTHER INFORMATION: Primer

<400> SEQUENCE: 10
caattcaatt caatttagat gagagtcttt tccagttcg                          39

<210> SEQ ID NO 11
<211> LENGTH: 1013
<212> TYPE: DNA
<213> ORGANISM: ARTIFICIAL SEQUENCE
<220> FEATURE:
<223> OTHER INFORMATION: Lactate dehydrogenase

<400> SEQUENCE: 11
cctaggatgg caactttaaa ggatcagctg attcagaatc ttctgaagga agaacatgtc    60
ccacagaata agattacaat tgttggtgtt ggtgctgttg gtatggcctg tgccatcagt   120
atcttaatga aggacttggc agatgaagtt gctcttgttg atgtcatgga agataaactg   180
aagggagaga tgatggattt acaacatggt tctcttttcc ttagaacacc aaaaattgtc   240
tctggtaaag actataatgt gacagcaaac tccagactgg ttattatcac agctggtgca   300
agacagcaag agggagagtc tagactgaat ttggttcaga gaaacgtgaa catctttaaa   360
ttcatcattc ctaatattgt aaaatactct ccaaattgta agttgcttgt tgtttccaat   420
ccagtcgata ttttgaccta tgtggcttgg aagataagtg gttttccaaa aacagagtt    480 attggaagtg gttgtaatct ggattcagct cgcttcagat atttaatggg tgagagactg   540
ggagttcatc cattatcttg tcatggttgg attcttggtg agcatggtga ctctagtgtg   600
cctgtatgga gtggagtgaa tgttgctggt gtctccctga gaatttaca tcctgaatta   660 ggaactgatg cagataagga acagtggaaa gctgttcata acaagtggt tgacagtgct   720 tatgaggtga tcaaactgaa aggatacaca tcctgggcca ttggactgtc agtggccgat   780
ttggcagaaa gtataatgaa gaatcttaga gagagtgcatc ctatttccac catgattaag   840
ggtttatatg gaataaaaga ggatgtcttc cttagtgttc cttgtatctt gggacagaat   900
ggaatctcag acgttgtgaa agtgactctg actcatgaag aagaggcatg tttgaagaag   960
agtgcagata cactttgggg aatccagaaa gaacttcagt tttaagcggc cgc        1013

<210> SEQ ID NO 12
<211> LENGTH: 42
<212> TYPE: DNA
<213> ORGANISM: ARTIFICIAL SEQUENCE
<220> FEATURE:
<223> OTHER INFORMATION: Primer

<400> SEQUENCE: 12
gaaaacgagc tcggctcgtg gaaaaaatga ataatttatg aa                      42

<210> SEQ ID NO 13
<211> LENGTH: 34
<212> TYPE: DNA
<213> ORGANISM: ARTIFICIAL SEQUENCE
<220> FEATURE:
<223> OTHER INFORMATION: Primer

<400> SEQUENCE: 13
cctaggccta ggtttgattg atttgactgt gtta                               34

<210> SEQ ID NO 14
<211> LENGTH: 34
<212> TYPE: DNA
```

<213> ORGANISM: ARTIFICIAL SEQUENCE
<220> FEATURE:
<223> OTHER INFORMATION: Primer

<400> SEQUENCE: 14
cctaggccta ggtttgattg atttgactgt gtta                      34

<210> SEQ ID NO 15
<211> LENGTH: 35
<212> TYPE: DNA
<213> ORGANISM: ARTIFICIAL SEQUENCE
<220> FEATURE:
<223> OTHER INFORMATION: Primer

<400> SEQUENCE: 15
ccaacactcg agttgagtaa ccattatttg tatcg                     35

<210> SEQ ID NO 16
<211> LENGTH: 59
<212> TYPE: DNA
<213> ORGANISM: ARTIFICIAL SEQUENCE
<220> FEATURE:
<223> OTHER INFORMATION: Primer

<400> SEQUENCE: 16
ttaaacaccg gtttaattaa gcggccgcga attcagtttt tgattaagcc ttctagtcc    59

<210> SEQ ID NO 17
<211> LENGTH: 32
<212> TYPE: DNA
<213> ORGANISM: ARTIFICIAL SEQUENCE
<220> FEATURE:
<223> OTHER INFORMATION: Primer

<400> SEQUENCE: 17
gtacatggat cccttcattg agcttagaac cc                        32

<210> SEQ ID NO 18
<211> LENGTH: 76
<212> TYPE: DNA
<213> ORGANISM: ARTIFICIAL SEQUENCE
<220> FEATURE:
<223> OTHER INFORMATION: Primer

<400> SEQUENCE: 18
ggatccggat ccataacttc gtataatgta tgctatacga agttatttcg agaactgctc    60
tgtttagctt gcctcg                                          76

<210> SEQ ID NO 19
<211> LENGTH: 76
<212> TYPE: DNA
<213> ORGANISM: ARTIFICIAL SEQUENCE
<220> FEATURE:
<223> OTHER INFORMATION: Primer

<400> SEQUENCE: 19
gagttcgtcg acataacttc gtatagcata cattatacga agttatgttt cgacactgg     60 atggcggcgt tagtat                                          76

<210> SEQ ID NO 20
<211> LENGTH: 1058
<212> TYPE: DNA
<213> ORGANISM: ARTIFICIAL SEQUENCE
<220> FEATURE:
<223> OTHER INFORMATION: Cre recombinase

<400> SEQUENCE: 20

```
cctaggccta ggatgtctaa tttattaacc gtacaccaaa atttgccagc attgccggtc    60
gatgcaactt ctgatgaggt tagaaagaac ttaatggaca tgttcaggga tagacaggct   120
ttttctgagc atacctggaa aatgttgttg tctgtttgca gatcatgggc tgcatggtgc   180
aagttgaata acagaaaatg gtttccagca gaacctgaag atgttagaga ttatttgttg   240
tatttgcagg ctagaggttt ggcagtaaaa actatccagc aacatttggg tcagttgaac   300
atgttgcata gaagatcagg tttgccaaga ccatctgact ctaatgctgt ttcattggtt   360
atgagaagaa tcagaaaaga aaacgttgat gctggtgaaa gagcaaaaca ggctttggct   420
tttgaaagaa ctgatttcga ccaggttaga tcattgatgg aaaattctga tagatgccag   480
gatataagaa atttggcatt tttgggtatt gcttataaca ccttgttaag aatagccgaa   540
attgccagga tcagggttaa agatatttca agaactgacg gtggtagaat gttaatccat   600
attggtagaa ctaaaacttt ggtttctacc gcaggtgtag agaaggcatt gtctttgggt   660
gtaactaaat tggtcgagag atggattttg gtctctggtg tagctgatga tccaaataac   720
tacttgtttt gcagagtcag aaaaaatggt gttgccgcac catctgccac ctctcagttg   780
tcaactagag ccttggaagg tatttttgaa gcaactcata gattgattta cggtgctaag   840
gatgactctg gtcagagata cttggcctgg tctggacact ctgccagagt cggagccgca   900
agagatatgg ctagagctgg agtttcaata ccagagatca tgcaagctgg tggttggacc   960
aatgtaaaca ttgtcatgaa ctatatcaga aacttggatt ctgaaacagg tgcaatggtc  1020
agattgttgg aagatggtga ttaggcggcc gcgcggcc                          1058
```

<210> SEQ ID NO 21
<211> LENGTH: 47
<212> TYPE: DNA
<213> ORGANISM: ARTIFICIAL SEQUENCE
<220> FEATURE:
<223> OTHER INFORMATION: Primer

<400> SEQUENCE: 21

```
gtaatccata tgttcgagaa ctgctctgtt tagcttgcct cgtcccc                  47
```

<210> SEQ ID NO 22
<211> LENGTH: 34
<212> TYPE: DNA
<213> ORGANISM: ARTIFICIAL SEQUENCE
<220> FEATURE:
<223> OTHER INFORMATION: Primer

<400> SEQUENCE: 22

```
gtaactgagc tcgttttcga cactggctgg cggc                                34
```

<210> SEQ ID NO 23
<211> LENGTH: 34
<212> TYPE: DNA
<213> ORGANISM: ARTIFICIAL SEQUENCE
<220> FEATURE:
<223> OTHER INFORMATION: Primer

<400> SEQUENCE: 23

```
gtaatcggat ccttcgagaa ctgctctgtt tagc                                34
```

<210> SEQ ID NO 24
<211> LENGTH: 34
<212> TYPE: DNA

```
<213> ORGANISM: ARTIFICIAL SEQUENCE
<220> FEATURE:
<223> OTHER INFORMATION: Primer

<400> SEQUENCE: 24
gtaactgtcg acgttttcga cactggatgg cggc                                34

<210> SEQ ID NO 25
<211> LENGTH: 32
<212> TYPE: DNA
<213> ORGANISM: ARTIFICIAL SEQUENCE
<220> FEATURE:
<223> OTHER INFORMATION: Primer

<400> SEQUENCE: 25
gagctcgagc tcacggatta gaagccgccg ag                                  32

<210> SEQ ID NO 26
<211> LENGTH: 35
<212> TYPE: DNA
<213> ORGANISM: ARTIFICIAL SEQUENCE
<220> FEATURE:
<223> OTHER INFORMATION: Primer

<400> SEQUENCE: 26
cctaggccta ggggttttttt ctccttgacg ttaaa                              35

<210> SEQ ID NO 27
<211> LENGTH: 37
<212> TYPE: DNA
<213> ORGANISM: ARTIFICIAL SEQUENCE
<220> FEATURE:
<223> OTHER INFORMATION: Primer

<400> SEQUENCE: 27
gtacatagat cagcccctgt gtgttctcgt tatgttg                             37

<210> SEQ ID NO 28
<211> LENGTH: 33
<212> TYPE: DNA
<213> ORGANISM: ARTIFICIAL SEQUENCE
<220> FEATURE:
<223> OTHER INFORMATION: Primer

<400> SEQUENCE: 28
gtacatagaa tattgcgaat accgcttcca caa                                 33

<210> SEQ ID NO 29
<211> LENGTH: 28
<212> TYPE: DNA
<213> ORGANISM: ARTIFICIAL SEQUENCE
<220> FEATURE:
<223> OTHER INFORMATION: Primer

<400> SEQUENCE: 29
ctgtcaagat cttgttggaa tagaaatc                                       28

<210> SEQ ID NO 30
<211> LENGTH: 30
<212> TYPE: DNA
<213> ORGANISM: ARTIFICIAL SEQUENCE
<220> FEATURE:
<223> OTHER INFORMATION: Primer

<400> SEQUENCE: 30
ctgtcacata tgaaatgggt gaatgttgag                                     30
```

```
<210> SEQ ID NO 31
<211> LENGTH: 28
<212> TYPE: DNA
<213> ORGANISM: ARTIFICIAL SEQUENCE
<220> FEATURE:
<223> OTHER INFORMATION: Primer

<400> SEQUENCE: 31
ctgtcaggat cctgttggaa tagaaatc                                              28

<210> SEQ ID NO 32
<211> LENGTH: 30
<212> TYPE: DNA
<213> ORGANISM: ARTIFICIAL SEQUENCE
<220> FEATURE:
<223> OTHER INFORMATION: Primer

<400> SEQUENCE: 32
ctgtcagtcg acaaatgggt gaatgttgag                                            30

<210> SEQ ID NO 33
<211> LENGTH: 31
<212> TYPE: DNA
<213> ORGANISM: ARTIFICIAL SEQUENCE
<220> FEATURE:
<223> OTHER INFORMATION: Primer

<400> SEQUENCE: 33
gaaaacgagc tcaacaagct catgcaaaga g                                          31

<210> SEQ ID NO 34
<211> LENGTH: 76
<212> TYPE: DNA
<213> ORGANISM: ARTIFICIAL SEQUENCE
<220> FEATURE:
<223> OTHER INFORMATION: Primer

<400> SEQUENCE: 34
catatgcata tgataacttc gtataatgta tgctatacga agttatttcg agaactgctc           60
tgtttagctt gcctcg                                                           76

<210> SEQ ID NO 35
<211> LENGTH: 76
<212> TYPE: DNA
<213> ORGANISM: ARTIFICIAL SEQUENCE
<220> FEATURE:
<223> OTHER INFORMATION: Primer

<400> SEQUENCE: 35
gagttcgagc tcataacttc gtatagcata cattatacga agttatgttt tcgacactgg           60
atggcggcgt tagtat                                                           76
```

YEAST STRAIN FOR LACTIC ACID PRODUCTION BY USING PENTOSE AND HEXOSE

FIELD OF THE INVENTION

The present invention relates to production of lactic acid, and in particular, to *Saccharomyces cerevisiae* and a method for producing lactic acid in high yield.

DESCRIPTION OF THE RELATED ART

In conventional production, lactic acid is obtained from fermentation of *Lactobacillus* spp., but a composite medium is required for culturing the *Lactobacillus* spp., which is costly, resulting in increased cost for separation and purification of lactic acid from a fermentation liquor, in addition to increased cost in the fermentation process. Since lactic acid plays a role as the monomer in the production of biodegradable polylactic acid, it is necessary to lower its production cost. Therefore, in many studies, an attempt to modify strains is initiated, for example, microbial fermentation by *Saccharomyces cerevisiae* to yield lactic acid. As a result of the native strains of *Saccharomyces cerevisiae* being not available for lactic fermentation, intra-cellular expression of exogenous lactate dehydrogenase (LDH) in *Saccharomyces cerevisiae* is carried out via genetic engineering by Dequin et al. in 1994, enabling *Saccharomyces cerevisiae* to produce lactic acid with fermentation of glucose (Biotechnology (New York), February 1994, 12: p. 173-177), and this is the first literature reporting production of lactic acid with yeast.

There are various biomass resources can be used as fermentation carbon sources, including sugar, starch and lignocellulose. The technologies for production of bioenergy and biomaterials such as lactic acid, organic acid or alcohol from sugar or starch materials as carbon sources for fermentation are well established; however, since supply pressure of foodstuff and cost of grains increase, production of bioenergy or biomaterials from sugar or starch materials is not economical and is undesired. Accordingly, production of bioenergy or biomaterials from lignocellulosic carbon sources actively developed in the industry.

Pentose is among primary constituents of hemicellulose, and the content of pentose is up to 30% of the plant fiber, so efficient utilization of xylose and conversion into target products are keys for using lignocellulosic carbon sources. Taking the development of the cellulosic ethanol industry as an example, the most widely used native *Saccharomyces cerevisiae* can not metabolize pentose sugars; therefore, from 1980s, the yeast or bacteria are modified by the scientists with genetic engineering or the method for adaptation of strains, to produce alcohol by fermentation of pentose such as xylose. Nancy Ho et al. firstly disclosed the method for preparing *Saccharomyces cerevisiae* (U.S. Pat. No. 5,789,210), solving the problems of culturing cost and mixed carbon sources, and the transgenic technologies are used by Nancy Ho et al. to enable the yeast to bear and express the genes of xylose reductase (XR), xylose dehydrogenase (XDH) and xylulokinase (XKS), and xylose is fermented with such recombinant yeast strains into alcohol.

In 2001 and 2002, it is respectively disclosed in Nature Works LLC (U.S. Pat. Nos. 7,109,010 and 7,141,410) that, the transgenic technologies are used to enable the native yeast strains, *Kluyveromyces* and *Candida sonorensis*, to express the exogenous lactate dehydrogenase, and allow it to ferment xylose into lactic acid but with low yield of only about 5% to 34%. In 2004, Cargill Inc (U.S. Pat. No. 7,943,366) disclosed that, by knockout of xylose reductase (XR) and xylose dehydrogenase (XDH), the original pentose metabolic genes of *Kluyveromyces marxianus* and *Candida sonorensis*, expressing instead xylulokinase (XKS) and exogenous xylose isomerase (XI) to enhance the ability of the yeasts to ferment xylose into lactic acid, the yield is up to 79%. This technology allows the yield of lactic acid to increase, but *Kluyveromyces marxianus* and *Candida sonorensis* are not the strains commonly used for fermentation.

In 2006, the native PDC1 and PDC5 genes of *Saccharomyces cerevisiae* are replaced with LDH by Takahashi et al., enabling the yeast strains to metabolize glucose into lactic acid; although its yield is up to 81.5%, this strain is slow in both growth and fermentation rate, taking 200 hours to reach top yield (Biosci Biotechnol Biochem. 2006 May; 70 (5): 1148-53), resulting in failure to meet with requirements for rapid production. In view of the above, for technologies of lactic acid production developed by modification of strains in the prior art, its yield or production process is improved; but for large-scale production, the available carbon sources are limited; therefore, it is still in need of the development of a strain with higher yield of lactic acid, and a production method with lower cost and higher yield of lactic acid.

SUMMARY OF THE INVENTION

The present invention provides a yeast for production of lactic acid with high yield, where modification of genes is used to enable *Saccharomyces cerevisiae* to ferment xylose into lactic acid with increased yield of up to about 80%, as a result of many advantages such as easy culturing and strong fermentability of *Saccharomyces cerevisiae*.

The present invention provides a biologically pure culture of microbial strain; wherein the microbial strain is derived from *Saccharomyces cerevisiae* FENC-05 and includes at least one set of exogenous lactate dehydrogenase gene, and the microbial strain produces lactic acid from carbon sources in yield of higher than about 75%; wherein the carbon sources include pentose and hexose, and the *Saccharomyces cerevisiae* FENC-05 is deposited in the Deutsche Sammlung von Mikroorganismen and Zellkulturen (DSMZ), with accession number DSM 25508.

The present invention also provides a method for preparing the biologically pure culture according to the invention, comprising transforming the exogenous lactate dehydrogenase gene into *Saccharomyces cerevisiae* FENC-05, and screening microbial strains which use carbon sources to produce lactic acid in yield of more than about 75%; wherein the carbon sources include pentose and hexose.

The present invention further provides a method for production of lactic acid, which is characterized in culturing the biologically pure culture of microbial strain according to the invention in a culture medium and obtaining lactic acid from the biologically pure culture; where the culture medium contains carbon sources, and the carbon sources include pentose and hexose.

The present invention is described in detail in the following sections. Other characteristics, purposes and advantages of the present invention can be easily found in the detailed description and claims.

BRIEF DESCRIPTION OF THE DRAWINGS

The invention will be described according to the appended drawings in which.

PREFERRED EMBODIMENT OF THE PRESENT INVENTION

Figure 1:
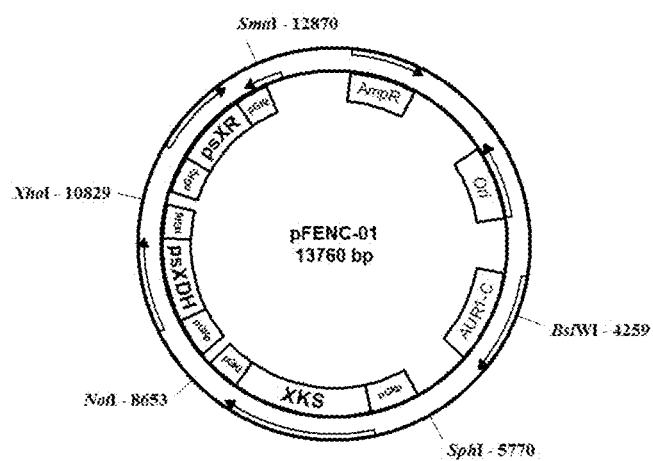
FIG. 1 shows a plasmid profile of pFENC-01.

The present invention can be more readily understood by reference to the following detailed description of various embodiments of the invention, the examples, and the chemical drawings and tables with their relevant descriptions. It is to be understood that unless otherwise specifically indicated by the claims, the invention is not limited to specific preparation methods, because as one of ordinary skill in the relevant arts is well aware, such things can, of course, vary. It is also to be understood that the terminology used herein is for the purpose of describing particular embodiments only and is not intended to be limiting.

As utilized in accordance with the present disclosure, the following terms, unless otherwise indicated, shall be understood to have the following meaning:

As used herein, the term "lactic acid" refers to 2-hydroxypropionic acid, which is an important compound in a variety of biochemical processes. Lactic acid is a carboxylic acid containing a hydroxyl group, with a molecular formula of $C_3H_6O_3$. Lactic acid has two optical isomers, with one being L-(+)-lactic acid or (S)-lactic acid and the other being D-(−)-lactic acid or (R)-lactic acid. In a preferred embodiment of the present invention, lactic acid refers to L-(+)-lactic acid or (S)-lactic acid.

As mentioned herein, the word "pure culture" refers to a culture only containing a microbe; and if a certain culture is produced by proliferation of a single microbial colony, it is called the pure culture of the microbe.

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint.

"Optional" or "optionally" means that the subsequently described event or circumstance may or may not occur, and that the description includes instances where said event or circumstance occurs and instances where it does not. For example, the phrase "optionally comprise an agent" means that the agent may or may not exist.

According to the present invention, the yield of lactic acid is measured by a general measuring method, specially, by high performance liquid chromatography (HPLC). As mentioned herein, the yield of lactic acid refers to a value obtained from centrifugation and filtration of the samples resulted from fermentation prior to quantification of the resulted filtrate by HPLC. HPLC is carried out for analysis under the following conditions: column: Transgenomics 87H column, column temperature set at 65° C., mobile phase: 5 mM $H_2SO_4$, and flow rate: 0.6 mL/min.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The present invention provides a biologically pure culture of microbial strain; wherein the microbial strain is derived from *Saccharomyces cerevisiae* FENC-05 and includes at least one set of exogenous lactate dehydrogenase gene, and the microbial strain produces lactic acid from carbon sources in yield of higher than about 75%; wherein the carbon sources include pentose and hexose, and the *Saccharomyces cerevisiae* FENC-05 is deposited in the Deutsche Sammlung von Mikroorganismen and Zellkulturen (DSMZ), with accession number DSM 25508.

As mentioned herein, the word "exogenous" refers to those which are not derived from wild species of *Saccharomyces cerevisiae*, i.e., which are not found in *Saccharomyces cerevisiae* in nature.

As mentioned herein, the word "lactate dehydrogenase gene" refers to one which encodes the product having activities of the lactate dehydrogenase, where the lactate dehydrogenase is capable of catalyzing conversion between pyruvic acid and lactic acid, or is capable of catalyzing conversion between the reduced nicotinamide adenine dinucleotide and the oxidized one. For lactic acid having two optical isomers, L-(+)-lactic acid and D-(−)-lactic acid, L-(+)-lactic acid is generated from L-lactate dehydrogenase, D-(−)-lactic acid is generated from D-lactate dehydrogenase, and it is preferable for the lactate dehydrogenase to be encoded by L-lactate dehydrogenase gene.

The exogenous lactate dehydrogenase gene according to the present invention may be an integral gene which has been or not decoded, or its functional fragments. In a preferred embodiment of the present invention, the exogenous lactate dehydrogenase gene is derived from bovine.

Each of species has its conventional nucleic acid codons for translation of amino acid sequence; therefore, for intracellular expression of exogenous gene, in the case of direct utilization of gene sequence of the original species, failure to recognize codons by the host cells will cause failure to transcribe and translate into protein. Accordingly, in a preferred embodiment of the present invention, with the lactate dehydrogenase gene encoding from bovine as template, the exogenous lactate dehydrogenase is artificially optimized by comparison with the conventional codon database of species. The lactate dehydrogenase gene encoding from bovine is modified into an artificial sequence readily recognized by the yeast cells and is shown in SEQ ID NO. 11. Therefore, this segment of gene encoding may express the lactate dehydrogenase protein having enzymatic functions in the yeast cell.

The exogenous lactate dehydrogenase gene according to the present invention may be initiated by the promoter owned by *Saccharomyces cerevisiae* or the exogenous promoter. Preferably, the exogenous lactate dehydrogenase is initiated by the promoter owned by *Saccharomyces cerevisiae*; more preferably, the exogenous lactate dehydrogenase is initiated by the promoter owned by *Saccharomyces cerevisiae* associated with utilization of carbon sources; and particularly preferably, the exogenous lactate dehydrogenase is regulated by pyruvate decarboxylase 1 promoter.

In the preferred embodiments of the present invention, the exogenous lactate dehydrogenase gene is substituted for the native pyruvate decarboxylase 1 structural gene in *Saccharomyces cerevisiae*, and is regulated by the integral pyruvate decarboxylase 1 promoter.

In a preferred embodiment of the present invention, the microbial strain *Saccharomyces cerevisiae* further comprises at least one set of pentose metabolic genes. Preferably, the pentose metabolic gene is selected from a group consisting of xylose reductase, xylose dehydrogenase, xylulokinase and xylose isomerase.

In a preferred embodiment of the present invention, the biologically pure culture contains *Saccharomyces cerevisiae* FENC-Sc 5dPL-4LK, deposited in the Deutsche Sammlung von Mikroorganismen and Zellkulturen (DSMZ) according to Budapest treaty, with accession number DSM 26705.

Compared to the parental strain FENC-05, the strain FENC-Sc 5dPL-4LK provides alcohol yield of only remaining 10% while lactic acid yield of up to 80% at the time of fermentation with carbon sources including pentose and hexose.

The present invention also provides a method for preparing the biologically pure culture according to the invention, comprising transforming the exogenous lactate dehydrogenase gene into *Saccharomyces cerevisiae* FENC-05, and screening microbial strains which use carbon sources to produce lactic acid in yield of more than about 75%; wherein the carbon sources include pentose and hexose.

In a preferred embodiment of the present invention, the method comprises knocking out pyruvate decarboxylase 1 from *Saccharomyces cerevisiae*, and regulating the exogenous lactate dehydrogenase gene by the pyruvate decarboxylase 1 promoter.

According to the present invention, the method for screening microbial strains with the lactic acid yield of more than about 75% may comprise directly measuring the lactic acid yield or screening the microbial strain having more sets of exogenous lactate dehydrogenase gene, and preferably, screening the microbial strain having more sets of exogenous lactate dehydrogenase genes. In a preferred embodiment of the present invention, screening is carried out in the culture medium containing calcium carbonate. Because the microbial strain having more sets of lactate dehydrogenase genes may generate much more lactic acid which can react with calcium carbonate to form calcium lactate having solubility higher than calcium carbonate, the original white culture medium containing calcium carbonate around the microbial colonies which may generate lactic acid will become transparent and form a clear zone. Accordingly, the microbial strain with higher yield of lactic acid will be obtained by selection of the microbial strain with bigger clear zone. On the other hand, the screening method may include transferring a reporter gene at the same time and measurement by measuring expression of the reporter gene. In a preferred embodiment of the present invention, the reporter gene is a drug resistance gene.

In the embodiments of the present invention, knockout of the native pyruvate decarboxylase 1 in *Saccharomyces cerevisiae* FENC-05 strain is carried out with simultaneous substitution of exogenous lactate dehydrogenase gene for original pyruvate decarboxylase gene such that expression of lactate dehydrogenase is regulated by the original pyruvate decarboxylase 1 promoter for obtaining the recombinant yeast strain FENC-5dPLK. Subsequently, the drug resistance gene of the strain is knocked out with the Cre/loxp system, to provide FENC-5dPL for transferring the exogenous lactate dehydrogenase again. The drug resistance gene accompanied by the exogenous lactate dehydrogenase is inserted into the yeast genome at random, and then the higher resistant strain is screened out in the culture medium containing high concentration of antibiotics, to select the yeast strain, i.e., FENC-Sc 5dPL-4LK, including more sets of lactate dehydrogenase genes.

The present invention further provides a method for production of lactic acid, which is characterized in culturing the biologically pure culture of microbial strain according to the invention in a culture medium and obtaining lactic acid from the biologically pure culture; where the culture medium contains carbon sources, and the carbon sources include pentose and hexose.

In the preferred embodiments of the present invention, the hexose is selected from a group consisting of glucose, fructose, galactose and mannose.

On the other hand, in the preferred embodiments of the present invention, the pentose is selected from a group consisting of xylose and arabinose.

The method according to the present invention may be carried out by those ordinarily skilled in the art for fermentation. It is preferred for culturing to be batch culturing or batch-feeding culturing. Formulation of the specific culture medium and determination of culturing conditions are decided by those ordinarily skilled in the art on a basis of disclosure in the specification of the present invention.

According to the present invention, lactic acid is present in the microbe or culture medium. The method according to the present invention further comprises a step of recovering lactic acid from the culture medium. Recovering is carried out in a manner well known by those ordinarily skilled in the art pertaining to the present invention.

The following examples are provided to aid those skilled in the art in practicing the present invention.

EXAMPLES

Cloning Gene Associated with Metabolism of Xylose and Construction of Recombinant Plasmid In this example, the gene associated with metabolism of xylose is cloned by polymerase chain reaction (PCR). Firstly, with a primer combination of SEQ ID NO. 1/SEQ ID NO. 2, SEQ ID NO. 3/SEQ ID NO. 4, and with a gene library extracted from *Saccharomyces cerevisiae* BCRC 22743 as template, the pGK promoter and pGK terminator are cloned; with a primer combination of SEQ ID NO. 5/SEQ ID NO. 6, SEQ ID NO. 7/SEQ ID NO. 8, the xylose reductase (XR) and xylose dehydrogenase (XDH) genes are cloned out of the *Pichia stipitis* cells; with a primer combination of SEQ ID NO. 9/SEQ ID NO. 10, and with a gene library extracted from *Saccharomyces cerevisiae* BCRC 22743 as template, the xylulokinase (XKS) gene is cloned by PCR; and the nucleic acid fragments from above are constructed together into the pAUR101 plasmid at appropriate restriction sites, finishing construction of xylose-related gene recombination vector and obtaining the plasmid pFENC-01 (as shown in FIG. 1).

Construction of the Plasmid pFENC-L01 having the PDC1 Gene Substituted for Lactate Dehydrogenase Gene (LDH)

With slight modification of the method of Takahashi et al. for construction of the transgenic vector, the LDH gene expression cassette is inserted into the yeast chromosome at the site of PDC1 (APPLIED AND ENVIRONMENTAL MICROBIOLOGY, April 2005, p. 1964-1970) as follows:

Synthesis of Lactate Dehydrogenase LDH Whole Gene

With the LDH gene encoding from bovine as template, by artificial treatment for optimization, and comparison with the conventional codon database, the LDH gene encoding from bovine is altered into the artificial sequence SEQ ID NO. 11 readily recognized by the yeast cells, such that this segment of gene encoding may express the LDH protein having enzymatic functions in the yeast cells.

Whole gene of lactate dehydrogenase is synthesized by PCR following the sequence SEQ ID No. 11.

Construction of Plasmid pFENC-L01 for Gene Substitution

Figure 2:
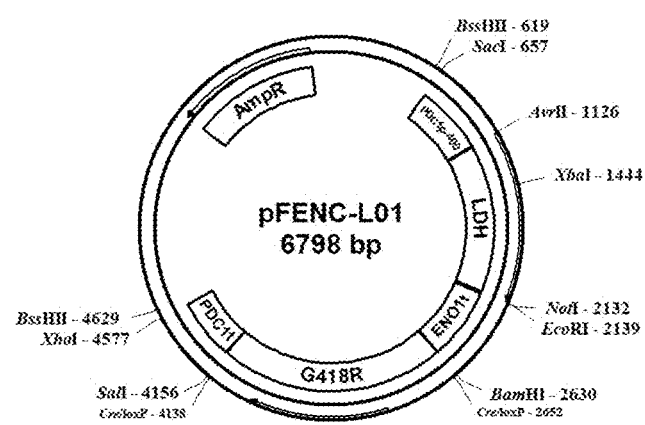
FIG. 2 shows a plasmid profile of pFENC-L01.

With a primer combination of SEQ ID NO. 12/SEQ ID NO. 13, SEQ ID NO. 14/SEQ ID NO. 15 and SEQ ID NO. 16/SEQ ID NO. 17 respectively, and with the gene library extracted from *Saccharomyces cerevisiae* BCRC 22743 as template, a fragment of PDC1 promoter (400 bp), a fragment of PDC1 terminator, and ENO1 terminator are cloned in part by PCR; with a primer combination of SEQ ID NO. 18/SEQ ID NO. 19, and with pFa-KanMX6 plasmid as template, the anti-G418 gene expression cassette is cloned by PCR, such that it carried the loxp sequence. The nucleic acid fragment, LDH gene fragment and vector pBluescript II KS (−) are joined at appropriate restriction sites, to provide the plasmid pFENC-L01 for gene substitution (as shown in FIG. 2).

Construction of the Recombinant Enzyme Expression Plasmid pFENC-Cre of Cre/loxp Gene-Knockout System With slight modification of the method of Hegemann et al., the yeast gene-knockout system is created (Nucleic Acids Research, 1996, Vol. 24, No. 13 2519-2524) as follows:

Synthesis of Recombinant Enzyme Cre Whole Gene

With Cre gene encoding from bacteriophage P1 (NCBI Reference Sequence: YP_006472.1) as template, with artificial treatment for optimization, and by comparison with conventional species codon database, the Cre gene encoding from bacteriophage P1 is altered into the artificial sequence SEQ ID NO. 20 readily recognized by the yeast cells, such that this segment of gene encoding may express the Cre protein having enzymatic functions in the yeast cells. Cre whole gene is synthesized by PCR following the sequence of SEQ ID NO. 20.

Construction of Recombinant Enzyme Cre Induced Expression Plasmid pFENC-Cre

Figure 3:
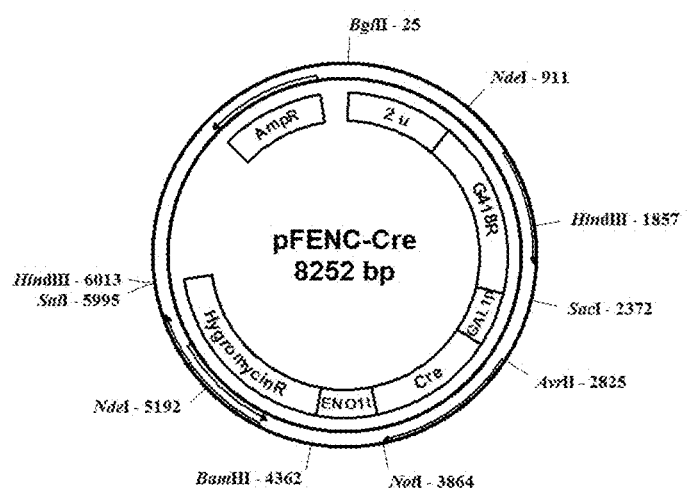
FIG. 3 shows a plasmid profile of pFENC-Cre.

With a primer combination of SEQ ID NO. 21/SEQ ID NO. 22, and with the pFa-KanMX6 plasmid as template, the anti-G418 gene expression cassette is cloned by PCR; with a primer combination of SEQ ID NO. 23/SEQ ID NO. 24, and with the pFa6a-Hyg plasmid as template, the anti-Hygromycine gene expression cassette is cloned by PCR; with a primer combination of SEQ ID NO. 25/SEQ ID NO. 26, and with the pYD1 (Invitrogen) plasmid as template, a fragment of the GAL1 promoter is cloned by PCR; with a primer combination of SEQ ID NO. 16/SEQ ID NO. 17 respectively, and with the gene library extracted from *Saccharomyces cerevisiae* BCRC 22743, the ENO1 terminator is cloned by PCR; with a primer combination of SEQ ID NO. 27/SEQ ID NO. 28, and with the pSos ColI (AgilentTeclmologies) plasmid as template, a fragment of 2 u ori is cloned by PCR. The nucleic acid fragment from above, Cre gene fragment and vector pUC19 are joined at appropriate restriction sites, to provide the recombinant enzyme Cre induced expression plasmid pFENC-Cre (as shown in FIG. 3).

Construction of the Lactate Dehydrogenase Gene LDH Expression Plasmid pFENC-L02

Figure 4:
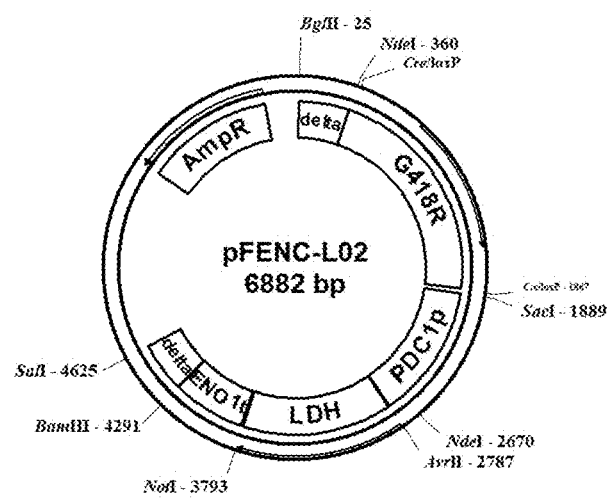
FIG. 4 shows a plasmid profile of pFENC-L02.

With a primer combination of SEQ ID NO. 29/SEQ ID NO. 30 and SEQ ID NO. 31/SEQ ID NO. 32, and with the gene library extracted from *Saccharomyces cerevisiae* BCRC22743, the yeast retrotransposon Delta sequence gene fragment is cloned by PCR; with a primer combination of SEQ ID NO. 33/SEQ ID NO. 13, and with the gene library extracted from *Saccharomyces cerevisiae* BCRC22743 as template, the integral PDC1 promoter (900 bp) is cloned by PCR; with a primer combination of SEQ ID NO. 34/SEQ ID NO. 35, and with the plasmid pFENC-L01 as template, the anti-G418 gene expression cassette is cloned by PCR; the plasmid pFENC-L01 is subject to enzyme restriction reaction by the restriction enzyme AvrII/BamHI, to give the LDH-ENO1 terminator; and the nucleic acid fragments from above and the vector pUC19 are joined at appropriate restriction sites, to give the plasmid pFENC-L02 (as shown in FIG. 4).

Construction of the Yeast Strain FENC-05 Enabling Simultaneous Metabolizing of Glucose and Xylose The pFENC-01 plasmid is transferred by chemistry into the industrial yeast strain *Saccharomyces cerevisiae* BCRC 22743 (Tranformation of yeast by the LiAC/SS carrier DNA/PEG method. Methods in Enzymology, 2002, 350, p. 87-96.); the transformed strain is screened in the YPD solid culture medium (1% yeast extract, 2% peptone, 2% glucose, 2% agar) including 0.5 μg/L Aureobasidin A and is placed at 30° C. for culturing; and from the transformed strains, the yeast strain FENC-05 having better ability for metabolism of pentose is selected, which is deposited in the Deutsche Sammlung von Mikroorganismen and Zellkulturen (DSMZ), with accession number DSM 25508.

Knockout of Native PDC1 Gene of FENC-05 While Simultaneous Replacing with LDH Gene at this Locus, Provides the Strain FENC-5dPL The Fragment from the Plasmid pFENC-L01 by Enzyme Restriction is Sent into the Cell of Yeast FENC-05 Via Electroporation.

The plasmid pFENC-L01 is subject to the enzyme restriction reaction by the restriction enzyme BssHII, the resulted nucleic acid fragment bearing the LDH gene is sent into the yeast cell via electroporation (1.5 kV, 200 ohm, 25 uF, 2 mm cuvette), and the transferred strain having resistance to G418 is screened in the YPD solid culture medium containing 300 μg/mL G418.

The Transgenic Strain having PDC1 Gene Substituted for LDH Gene is Screened in the Calcium Carbonate-Containing Culture Medium.

The transgenic strain having resistance to G418 is transferred into the YPD solid culture medium containing 0.5% calcium carbonate for culturing, and because there is only a portion of PDC1 promoter (400 bp) in the BssHII enzyme restricted pFENC-L01 fragment, which is not sufficient to drive LDH expression, only the transgenic strain having the native PDC1 sequence already substituted by the LDH gene can allow its LDH gene to be regulated by the integral native PDC1 promoter sequence for expression and to generate lactic acid and formation of the clear zone on the calcium carbonate-containing culture medium. The strain 5dP5LK-10 causing the clear zone is cultured for sporulation as follows: it is firstly cultured in the YPK culture medium (20 g/L peptone, 10 g/L yeast extract, 10 g/L KAc) for 16 hours, and then transferred into the SPM culture medium (10 g/L KAc, 1 g/L yeast extract, 0.5 g/L glucose, 0.05 g/L adenosine, 0.05 g/L uridine, 0.1 g/L tryptoophan, 0.1 g/L leucine, 0.1 g/L histidine) for culturing for 5 to 7 days at 30° C. for sporulation; the SPM liquor is plated onto the YPD solid culture medium for selection of single colony; the single colony is transferred into the YPD solid culture medium containing 0.5% calcium carbonate for culturing; and the strain having bigger clear zone is selected, indicating that two sets of PDC1 genes on its genome had already replaced by the LDH gene, with the strain being 5dP5LK-10S8.

The Drug Resistance Gene is Removed from the 5dP5LK-10S8 Strain by the Cre/loxP System, Creating the Strain FENC-5dPL.

The plasmid pFENC-Cre is transferred into the 5dP5LK-10S8 via electroporation; the successfully transgenic strain is screened in the YPD solid culture medium containing 300 μg/mL Hygromycin; the transgenic strain is cultured in the 2% SG solid culture medium (20 g/L galactose, 6.7 g/L YNB, 20 g/L agar) for induction of Cre expression and removal of G418-resistant gene. The colonies grown from the 2% SG culture medium are respectively transferred into the YPD solid culture mediums containing 300 μg/mL G418 or 300 μg/mL Hygromycin, confirming its failure to grow, indicating that the G418-resistant gene removal and pFENC-Cre deletion are completed, to provide the strain FENC-5dPL.

Construction of the Strain FENC-Sc 5dPL-4LK with High Level of LDH Expression

The Plasmid pFENC-L02 Restriction Fragments are Transferred into the Cells of the Yeast FENC-5dPL Via Electroporation.

The plasmid pFENC-L02 is subject to enzyme restriction with the restriction enzyme XhoI; the nucleic acid fragment bearing LDH gene encoding is transferred into the FENC-5dPL cell via electroporation (1.5 kV, 200 ohm, 25 uF, 2 mm cuvette), and the transgenic strain having resistance to G418 of high concentration is screened in the YPD solid culture medium containing 4000 μg/mL G418.

The Transgenic Strain which Might be Characterized by High Level of LDH Expression and High Yield of Lactic Acid is Screened in the Calcium Carbonate-Containing Culture Medium.

The transgenic strain having resistance to G418 of high concentration is transferred into the calcium carbonate-containing culture medium for culturing, and the transgenic strain FENC-Sc 5dPL-4LK with bigger clear zone than that of FENC-5dPL is selected.

Efficacy Demonstration:

Testing for FENC-5dPL Fermentation:

1. pre-culturing 1: single colonies are selected, and cultured in 2 mL YPD (10 g/L yeast extract; 20 g/L peptone; 20 g/L glucose) for 7 hours, at 30° C., and 200 rpm.

2. pre-culturing 2: the liquor from pre-culturing 1 is poured into the 100 mL YPD60 (10 g/L yeast extract; 20 g/L peptone; 60 g/L glucose) and cultured for 24 hours at 30° C. and 200 rpm.

3. preparation of microbe: the liquor from pre-culturing 2 is centrifuged at 8000 rpm, with the culture medium being removed; is rinsed twice with the ddH$_2$O, and further suspended into the 5 mL ddH$_2$O, for measurement of OD$_{600}$.

4. fermentation: volume of the fermentation liquor is 100 mL (60 g/L glucose, 35 g/L xylose, 1 g/L urea); in the group of FENC-5dPL, 3% calcium carbonate is additionally added. An appropriate amount of microbial suspension is inoculated into the fermentation liquor at OD 12, and cultured for 72 hours with sealing by a air lock, at 30° C. and 200 rpm.

5. analysis of components in the fermentation liquor:

(1) 1 mL fermentation liquor is taken out at the time points and centrifuged at 13,200 rpm, and the supernatant is filtrated through the 0.22 μm/PVDF sterile disposable filter prior to 1:5 dilution in the ddH$_2$O.

(2) HPLC analysis: Transgenomics 87H column 65° C., 5 mM H$_2$SO$_4$, 0.6 mL/min.

(3) yield calculated by: (product concentration/total of initial sugar amount)×100%, with the results shown in table 1 and table 2.

TABLE 1 amount of products from fermentation

|  |  | Glucose | Xylose | Xylitol | Lactic acid | Glycerol | Ethanol |
|---|---|---|---|---|---|---|---|
| 0 hr | FENC-05 | 60.29 | 34.77 |  |  |  |  |
|  | FENC-5dPL | 61.95 | 36.15 |  |  |  |  |

TABLE 1-continued amount of products from fermentation

|  |  | Glucose | Xylose | Xylitol | Lactic acid | Glycerol | Ethanol |
|---|---|---|---|---|---|---|---|
| 24 hr | FENC-05 |  | 2.82 | 9.42 |  | 35.67 | 4.85 |
|  | FENC-5dPL |  | 19.24 | 1.59 | 43.73 | 10.49 | 3.81 |
| 48 hr | FENC-05 |  |  | 9.26 |  | 36.56 | 4.87 |
|  | FENC-5dPL |  | 4.01 | 2.27 | 57.69 | 10.06 | 3.89 |
| 72 hr | FENC-05 |  |  | 8.26 |  | 35.63 | 4.73 |
|  | FENC-5dPL |  | 2.55 |  | 61.54 | 9.12 | 3.93 |

Unit: g/L

TABLE 2 yield

| | Yield (%) | |
|---|---|---|
|  | Lactic acid | Ethanol |
| FENC-05 | — | 75.0 |
| FENC-5dPL | 62.7 | 18.6 |

Demonstration of Expression Level of FENC-Sc 5dPL-4LK Lactate Dehydrogenase Protein Preparation of Microbe:

The single colonies are selected and cultured in 3 mL YPD at 30° C. and 200 rpm overnight; the 1 mL OD1 liquor is centrifuged for 1 minute at 4° C. and 13,200 rpm for removal of supernatant, and then the microbes are suspended in 100 μL 2× protein sample buffer, and heated for 20 minutes at 95° C. for preparation of samples.

Analysis of Level of Protein Expression

The 15 μL sample is analyzed by 8% SDS-PAGE, and classified into two groups.

Total protein: after electrophoresis, the SDS-PAGE is rinsed with water and stained with InstantBlue. Then total protein extraction amounts from each of samples are compared.

Figure 5:
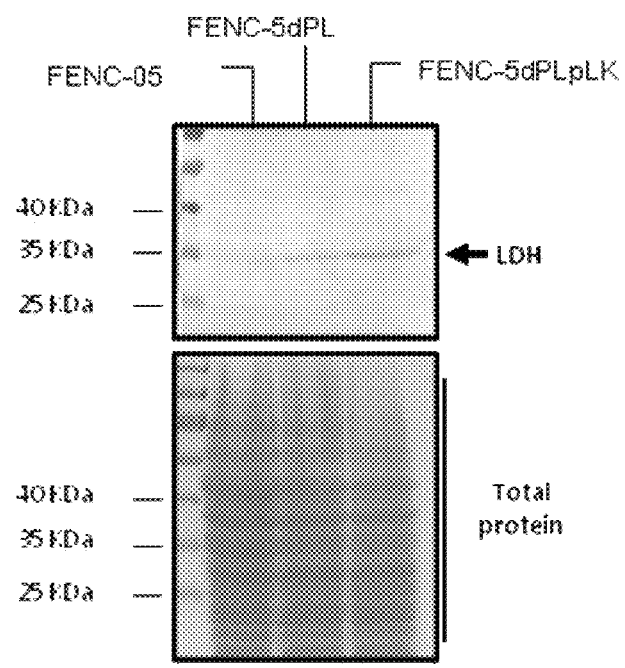
FIG. 5 shows a protein electrophoretogram and Western blotting of lactate dehydrogenase protein of FENC-Sc 5dPL-4LK.

LDH protein: after electrophoresis, the SDS-PAGE is subjected to PVDF transferring (15 V, 100 mA, 60 min), and the transferred PVDF film is soaked for 1 hour in the 5% skimmed milk powder (1×PBS) at room temperature, and then is soaked with the LDH primary antibody (sc-33781, Santa Cruz) solution (1:500, in 0.25% skimmed milk powder) at 4° C. overnight; rinsed in 1×PBS for three times, prior to addition of the secondary antibody (1:2500; 4142521f, NICHIREI BIOSCIENCES) for soaking for 1 hour at room temperature; rinsed in 1×PBS for three times, prior to addition of 1 mL NBT/BCIP for development, with its results shown in FIG. 5.

Testing for FENC-Sc 5dPL-4LK Fermentation 1. pre-culturing 1: single colonies are selected, and cultured for 7 hours in 2 mL YPD at 30° C. and 200 rpm.

2. pre-culturing 2: the liquor from pre-culturing 1 is poured into 100 mL YPD60 and cultured for 24 hours at 30° C. and 200 rpm.

3. preparation of microbe: the liquor from pre-culturing 2 is centrifuged at 8000 rpm, with the culture medium being removed; is rinsed twice with the secondary water, and further suspended into the 5 mL ddH$_2$O, for measurement of OD$_{600}$.

4. fermentation: volume of the fermentation liquor is 100 mL (60 g/L glucose, 35 g/L xylose, 1 g/L urea, 5% calcium carbonate). An appropriate amount of microbe suspension is inoculated into the fermentation liquor at OD 12, and cultured for 72 hours with sealing by a air lock, at 30° C. and 200 rpm.

5. analysis of components in the fermentation liquor:

(1) 1 mL fermentation liquor is taken out at the time points and centrifuged at 13,200 rpm, and the supernatant is filtrated through the 0.22 μm/PVDF sterile disposable filter prior to 1:5 dilution in the dd$H_2O$.

(2) HPLC analysis: Transgenomics 87H column 65° C., 5 mM $H_2SO_4$, 0.6 mL/min.

(3) yield calculated by: (product concentration/total of initial sugar amount)×100%, with the results shown in table 3 and table 4.

TABLE 3

| | | amount of products from fermentation | | | | | |
|---|---|---|---|---|---|---|---|
| | | Glucose | Xylose | Xylitol | Lactic acid | Glycerol | Ethanol |
| 0 hr | FENC-5dPL | 61.95 | 35.09 | | 0.71 | | 0.35 |
| | FENC-Sc 5dPL-4LK | 62.34 | 35.19 | | 0.79 | | 0.00 |
| 24 hr | FENC-5dPL | | 18.29 | 2.32 | 44.82 | 3.32 | 11.55 |
| | FENC-Sc 5dPL-4LK | | 25.56 | 0.68 | 57.15 | 1.86 | 4.42 |
| 48 hr | FENC-5dPL | | 5.04 | 3.65 | 56.58 | 3.36 | 11.02 |
| | FENC-Sc 5dPL-4LK | | 10.51 | 1.23 | 70.89 | 1.92 | 3.73 |
| 72 hr | FENC-5dPL | | 0.27 | 4.14 | 61.13 | 3.37 | 10.64 |
| | FENC-Sc 5dPL-4LK | | 0.73 | 1.50 | 79.53 | 2.03 | 2.37 |

Unit: g/L

TABLE 4

| | yield | |
|---|---|---|
| | Yield (%) | |
| | Lactic acid | Ethanol |
| FENC-5dPL | 62.3 | 21.2 |
| FENC-Sc 5dPL-4LK | 80.7 | 9.1 |

While the present invention has been described in conjunction with the specific embodiments set forth above, many alternatives thereto and modifications and variations thereof will be apparent to those of ordinary skill in the art. All such alternatives, modifications and variations are regarded as falling within the scope of the present invention.

What is claimed is:

1. A *Saccharomyces cerevisiae* yeast cell comprising an exogenous lactate dehydrogenase gene having the nucleotide sequence of SEQ ID NO: 11, wherein the yeast cell is capable of producing lactic acid from carbon sources comprising pentose and hexose with a yield of greater than about 75%.

2. The yeast cell according to claim 1, wherein the exogenous lactate dehydrogenase gene is operationally linked to a promoter of a pyruvate decarboxylase 1 gene.

3. The yeast cell according to claim 1, wherein the microbial strain further comprises at least one gene involved in pentose metabolism.

4. The yeast cell according to claim 3, wherein the at least one gene is selected from the group consisting of a xylose reductase gene, a xylose dehydrogenase gene, a xylulokinase gene, and a xylose isomerase gene.

5. The yeast cell according to claim 1, wherein the yeast cell is from *Saccharomyces cerevisiae* strain FENC-Sc 5dPL-4LK deposited with the depositary Deutsche Sammlung von Mikroorganismen and Zellkulturen (DSMZ) under accession number DSM 26705.

6. A method for preparing the yeast cell according to claim 1, comprising transforming *Saccharomyces cerevisiae* cells with at least one exogenous lactate dehydrogenase gene having the nucleotide sequence of SEQ ID NO. 11, and selecting transformed cells that produce lactic acid on a substrate comprising pentose and hexose with a yield that is greater than about 75%.

7. The method according to claim 6, which comprises knocking out a pyruvate decarboxylase 1 gene present in the *Saccharomyces cerevisiae* cells, wherein the pyruvate decarboxylase 1 gene comprises a promoter, and the method comprises placing the exogenous lactate dehydrogenase gene under control of the promoter.

8. A method for the production of lactic acid, comprising culturing the yeast cell according to claim 1 in a culture medium comprising pentose and hexose as carbon sources to produce lactic acid.

9. The method according to claim 8, wherein the hexose is selected from the group consisting of glucose, fructose, galactose and mannose.

10. The method according to claim 8, wherein the pentose is selected from the group consisting of xylose and arabinose.

11. The method according to claim 8, further comprising recovering lactic acid from the culture medium.

\* \* \* \* \*